United States Patent
Sandkamp et al.

(10) Patent No.: US 7,331,711 B2
(45) Date of Patent: Feb. 19, 2008

(54) METHOD AND FOOT SWITCH CONTROL FOR FAST ANGULATION CHANGES IN AN X-RAY SYSTEM

(75) Inventors: Bernhard Sandkamp, Erlangen (DE); Jan Bocse, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/415,743

(22) Filed: May 2, 2006

(65) Prior Publication Data
US 2007/0269011 A1  Nov. 22, 2007

(51) Int. Cl.
*H01G 1/02* (2006.01)
*H01G 1/56* (2006.01)

(52) U.S. Cl. .................. 378/197; 378/114
(58) Field of Classification Search ............. 378/37, 378/114, 195–198, 191, 208, 209
See application file for complete search history.

(56) References Cited

U.S. PATENT DOCUMENTS

| | | | |
|---|---|---|---|
| 5,185,778 A * | 2/1993 | Magram ............. | 378/196 |
| 5,590,166 A * | 12/1996 | Suni et al. ......... | 378/37 |
| 5,835,556 A * | 11/1998 | Rogalla et al. ..... | 378/195 |
| 5,997,176 A * | 12/1999 | Fairleigh .......... | 378/196 |
| 6,051,797 A * | 4/2000 | Meinel ............. | 200/86.5 |
| 6,234,672 B1 * | 5/2001 | Tomasetti et al. ... | 378/197 |
| 6,543,936 B2 * | 4/2003 | Feldman ........... | 378/191 |
| 6,823,207 B1 * | 11/2004 | Jensen et al. ...... | 600/427 |
| 2005/0094770 A1 * | 5/2005 | Fadler et al. ...... | 378/197 |
| 2005/0100134 A1 * | 5/2005 | Bauer et al. ....... | 378/197 |
| 2005/0117710 A1 * | 6/2005 | Heinze et al. ...... | 378/197 |
| 2006/0215817 A1 * | 9/2006 | Watanabe .......... | 378/114 |

\* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

In a method for fast angulation changes in a C-arm x-ray system, and a foot switch for effecting such fast angulation, a pedal of the foot switch that normally has a function not related to angulation of the C-arm is either permanently, or temporarily programmed, to operate as a pedal that, when depressed, automatically moves the C-arm to a predetermined angulation. The pedal can be movable between two positions, in order to selectively, automatically move the C-arm to either of two predetermined angulation positions, or can be used in conjunction with another pedal for that purpose. The pedal can also be temporarily given a security function and/or a radiation triggering function.

12 Claims, 4 Drawing Sheets

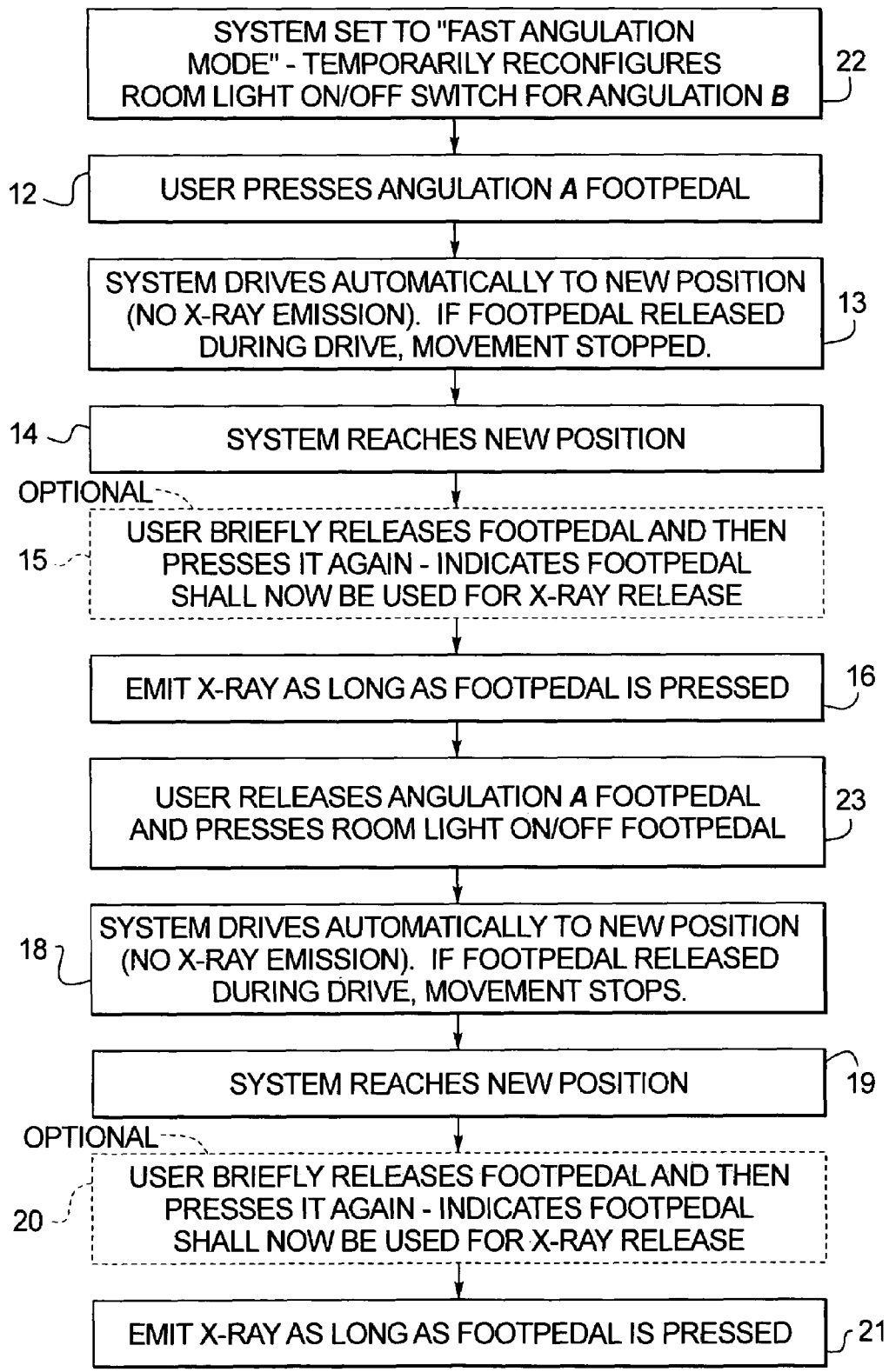

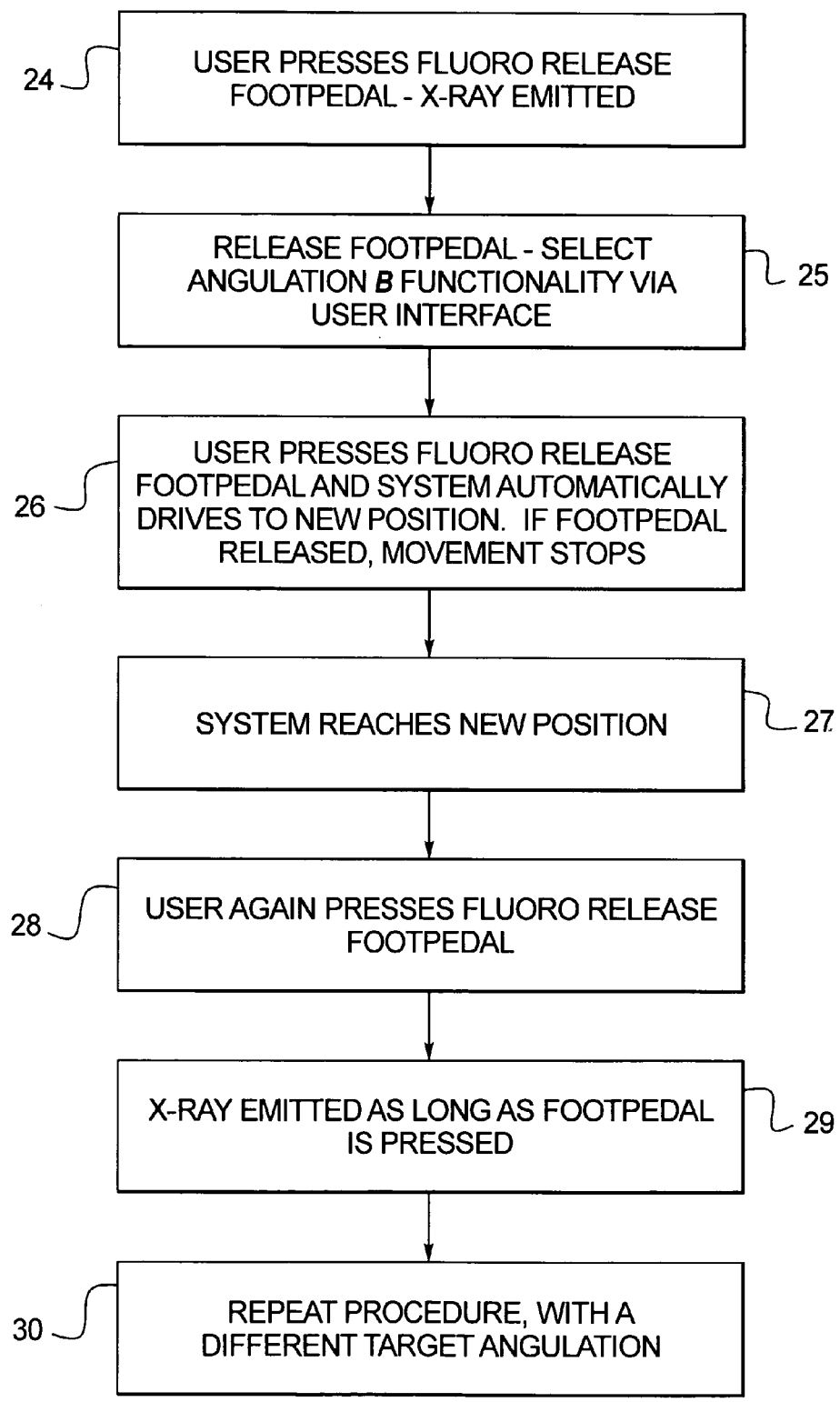

METHOD AND FOOT SWITCH CONTROL FOR FAST ANGULATION CHANGES IN AN X-RAY SYSTEM

BACKGROUND OF THE INVENTION

1. Field of the Invention

The present invention relates to a method for effecting fast angulation changes of the C-arm of an x-ray system, as well as to a foot switch control for effecting such fast angulation changes.

2. Description of the Prior Art

X-ray systems are commonly used for medical diagnostic purposes as well as medical interventional procedures that have an x-ray source (x-ray tube) that emits x-ray radiation that penetrates an examination subject and is detected by a radiation detector disposed opposite to the x-ray source. The x-ray source and the radiation detector are movable relative to the patient, such as by being mounted on a rotatable C-arm or some other type of movement-facilitating mechanism. The angle that a center ray, emitted by the x-ray source and proceeding to the radiation detector, makes with respect to a predetermined axis, usually the vertical axis, is defined as the angulation of the x-ray system, and this angulation determines the viewing direction from which the x-ray exposure will be obtained.

An example of such an x-ray system is the AXIOM Artis dWA biplane angiography system commercially available from Siemens Medical Systems. In this known biplane system, a first x-ray source and a first radiation detector are mounted on a first C-arm, and a second x-ray source and a second x-ray detector are mounted on a second C-arm so that a 3D image can be constructed from the images obtained in two intersecting planes by the two C-arm-mounted systems.

Another example of such a system is the AXIOM Artis dTA System, also commercially available from Siemens Medical Systems. This is a monoplane system having a single universally adjustable C-arm on which the x-ray source and the radiation detector are mounted.

In examinations and procedures of the type described above, it is frequently necessary to bring instruments such as catheters, guide wires, stents, etc., into the target (imaged) region. For this purpose, generation of an x-ray image in which both the anatomy and the instrument itself are visible is very helpful. Monoplane systems, however, can supply only two-dimensional images, and therefore correctly positioning the x-ray system in space to generate a two-dimensional image that captures all of the desired information can be difficult for the physician.

In general, x-ray systems allow the angulation to be freely adjusted within certain limitations. The position of the x-ray tube and the radiation detector are changed relative to the patient, so that a substantially arbitrary viewing direction can be selected. The physician conducting the examination or the procedure can control the angulation to switch back and forth between multiple viewing directions, so that the physician can obtain the necessary spatial impression of the position of the instruments in space.

Different ways for allowing the physician to control the angulation, and operate other features of an x-ray system, are known, including levers, push buttons, computer interfaces and foot switches. A foot switch of the type used in the above commercially available systems is disclosed in U.S. Pat. No. 6,051,797, the teachings of which are incorporated herein by reference. That foot switch has a number of foot pedals thereon and is connected to a computerized control for the x-ray system so that each foot pedal of the foot switch has a permanently associated function that is activated, deactivated or controlled by a predetermined movement of the foot pedal such as pressing the foot pedal, releasing the foot pedal and, in the case of a pivotable foot pedal controlling the degree and direction of pivoting of that foot pedal.

In addition, it is common for one of the pedals to be associated with a "dead man" function, meaning that as long as this foot pedal remains pressed, a particular function, such as movement of the C-arm, is inhibited.

In the case of a system having a single x-ray and radiation detector (monoplane system), a typical procedure for changing the angulation includes stopping the radiation emission by releasing the radiation pedal, releasing the securing of the C-arm by releasing the "dead man" pedal, approaching the new angulation by operating a joy stick, and after achieving the target angulation, again pressing the radiation pedal to obtain images from the new perspective.

It is also known to associate pre-programmed positions of various components of the x-ray system with particular switch positions or switch actuations. Even with such pre-programmed assistance, changing the angulation still involves stopping the radiation emission by releasing the radiation pedal, making a selection from a list of the pre-programmed positions and selecting a target angulation, actuating a control element, such as the joy stick, to initiate automatic positioning of the system to the target angulation, and after achieving the target angulation, pressing the radiation pedal to obtain images from the new perspective.

As noted above, biplane systems are also known. In such systems, the positions of the respective planes of the two x-ray tube/detector pairs are automatically selected, and the physician only switches back and forth between obtaining images in the two planes. These systems, however, are significantly more expensive than monoplane systems. Moreover, the view is limited to two viewing directions, and access to the patient is made more difficult by the presence of the second x-ray system.

SUMMARY OF THE INVENTION

It is an object of the present invention to simplify by making angulation changes in a monoplane x-ray system.

The above object is achieved in accordance with the present invention by a method and a foot switch control for a monoplane C-arm system making use of a foot switch for controlling the system wherein, by appropriate actuation of foot pedals of the foot switch, at least one foot pedal is temporarily relieved of its usual control function, and is used for angulation control. When the target angulation has been reached, this pedal is again restored to control its usual function.

For example, the foot pedal of a foot switch that is normally used to control radiation triggering can be temporarily used to control angulation, such as by setting the angulation to a predetermined angle, since during adjustment of the angulation the function of radiation triggering is not needed.

Another example of a conventionally-present foot pedal on a foot switch control that can be used for this purpose is the foot pedal that is used as the on/off switch for the room light. The temporary change in the function of one of the foot pedals can be accomplished by actuating that foot pedal in a particular sequence in relation to other foot pedals, or by a rapid pressing, release and re-pressing of the pedal, or by making an entry into the computerized control system via some other user interface available to the physician, such as via a touch screen display, a keyboard, a mouse, or the like.

DESCRIPTION OF THE DRAWINGS

FIG. 5 is a flow chart illustrating an exemplary embodiment of a manner of operating the apparatus shown in FIG. 1 using the foot switch shown in FIG. 4.

FIG. 6 is a flow chart of a further embodiment of a manner of operating the apparatus of FIG. 1 with a foot switch in accordance with the present invention.

DESCRIPTION OF THE PREFERRED EMBODIMENTS

Figure 1:
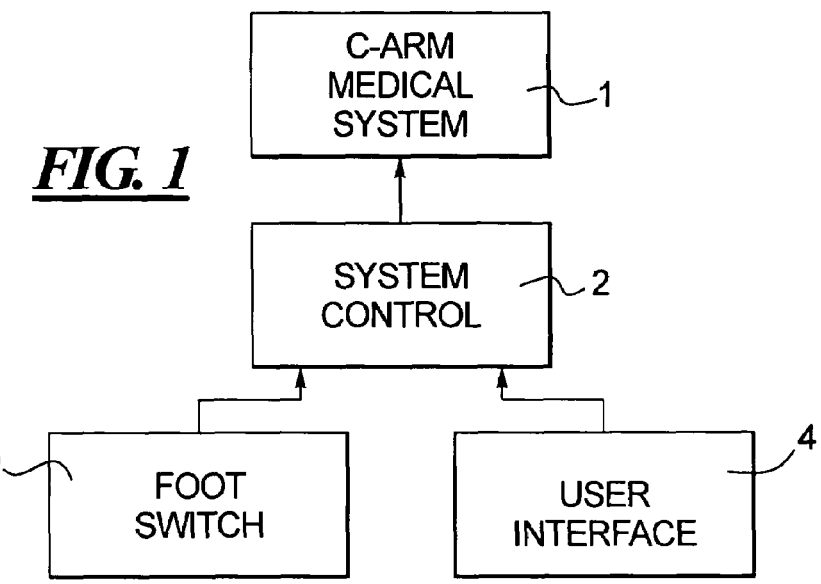
FIG. 1 is a block diagram showing the basic components of an apparatus operating according to the present invention.

FIG. 1 illustrates the basic components for operating a medical system 1 in accordance with the present invention. The medical system 1 may be, for example, a biplane angiography system. The medical system 1 is operated by a computerized system control, to which operating commands can be provided via a flip switch 3 and a separate user interface 4, such a keyboard, mouse, touch display, etc.

Figure 2:
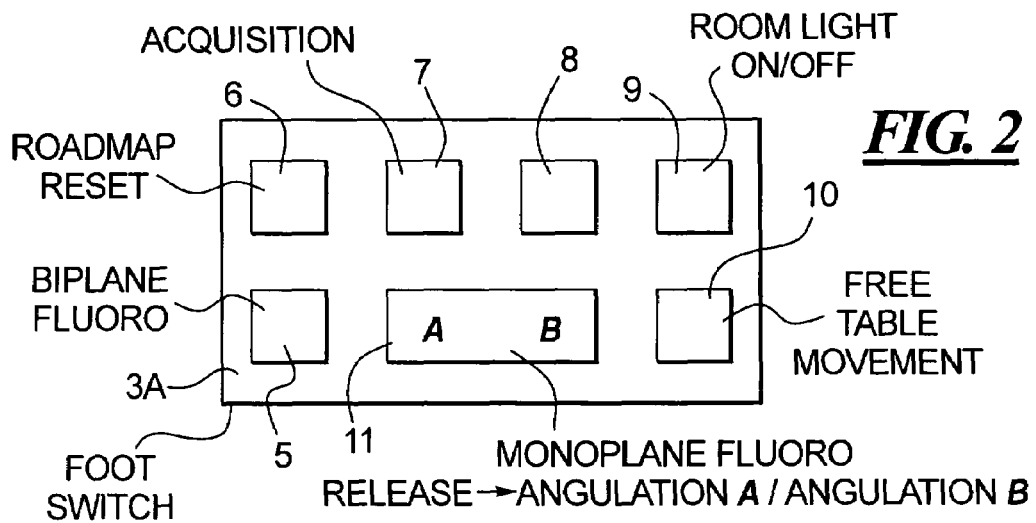
FIG. 2 schematically illustrates the functions assigned to various foot pedals of a foot switch in accordance with the present invention.

A first embodiment of the foot switch 3A in accordance with the invention is shown in FIG. 2. This embodiment of the foot switch 3A has a conventional arrangement of foot pedals, that include a food pedal 5 for biplane fluoro, a foot pedal 6 for roadmap reset, a foot pedal 7 for image acquisition that, when depressed, triggers emission of x-rays, a foot pedal 8 that can be used or not used as needed, a foot pedal 9 that controls the room light (on/off), and a foot pedal 10 that freeze (releases or enables) movement of the table on which the patient is lying.

A foot switch of the type shown in FIG. 2 conventionally has a pedal 11 for monoplane fluoro release. In accordance with the invention, the foot pedal 11 is either permanently used to control the angulations in the biplane angiography system, for example by depressing the side of the pedal 11 indicated A for the adjustment RAO=−35°, and depressing the side of the pedal 11 designated B for the adjustment RAO=+12°. The precise angulation adjustment that takes place by depressing side A or side B of the pedal 11 can be entered into the system control via the user interface 4. The positions associated with the respective sides A and B of the foot pedal 11 are thereby preprogrammed.

In addition to preprogramming the angulations of the C-arm in the biplane medical system 1, other functions associated with the foot pedal 11 can be preprogrammed as well. For example, it may be known that at the angulation A, the patient attenuation exhibits a value that is equivalent to 40 cm of water, but at the angulation B the patient exhibits an attenuation of only 25 cm of water. The voltage or current supply to the x-ray tube can be accordingly automatically adjusted at the respective angulations A and B so that there is no fluctuation between the images respectively generated at those different angulations.

Figure 3:
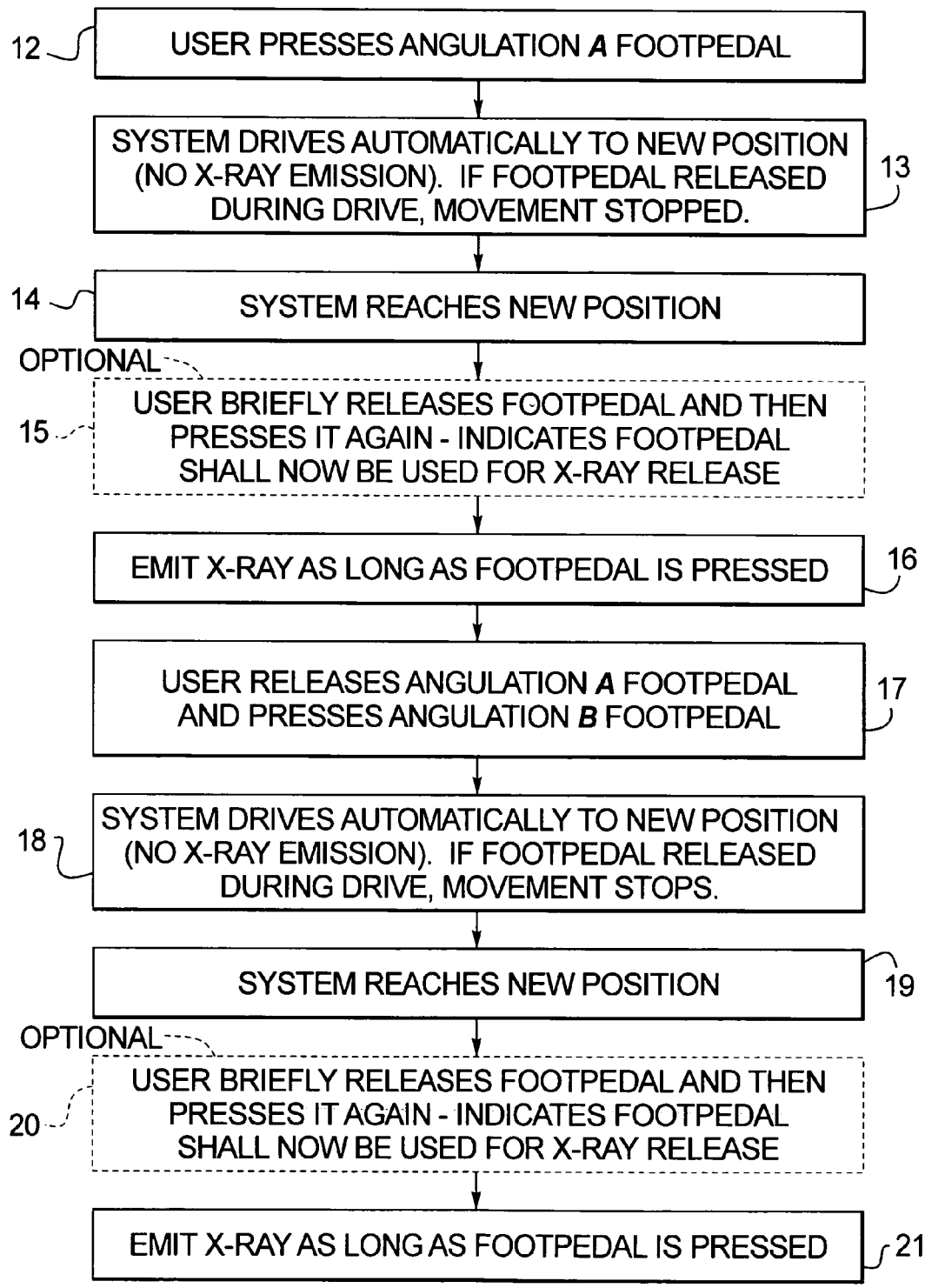
FIG. 3 is a flow chart of an exemplary embodiment of a manner of operating the apparatus of FIG. 1 using the foot switch shown in FIG. 2.

An example of the operation of the medical system 1, as a biplane angiography system, using the embodiment of the foot switch 3A of FIG. 2 will be explained using FIG. 3. First, operation will be explained without the optional steps 15 and 20.

In step 12, the user (operator) presses the angulation A foot pedal. As indicated in step 13, this causes the system 1 to automatically drive to a new position, with no x-ray emission occurring while the C-arm is moving. If foot pedal 11 is released during this drive, movement is automatically stopped. In step 14, the system (C-arm) reaches the new position that is preprogrammed to be associated with angulation A.

In step 16, x-rays are emitted as long as foot pedal 11 is pressed. In step 17, the user releases the angulation A foot pedal and presses the angulation B foot pedal. As indicated in step 18, this causes the system 1 (i.e., the C-arm thereof) to be automatically driven to a new position, preprogrammed to be associated with angulation B. Again, no x-ray emission occurs while the C-arm is moving, and if the foot pedal 11 is released before the C-arm reaches the position preprogrammed to be associated with angulation B, movement automatically stops.

As indicated in step 19, the system 1 reaches the new position and, as indicated in step 21, x-rays are emitted with the C-arm at angulation B as long as foot pedal 11 is depressed.

As indicated in optional steps 15 and 20, after the system has reached the angulation A position and after the system has reached the angulation B position, the user can briefly release the foot pedal 11 and then press it again. This indicates to the system control 2 that the foot pedal 11 shall now be used for x-ray release.

Figure 4:
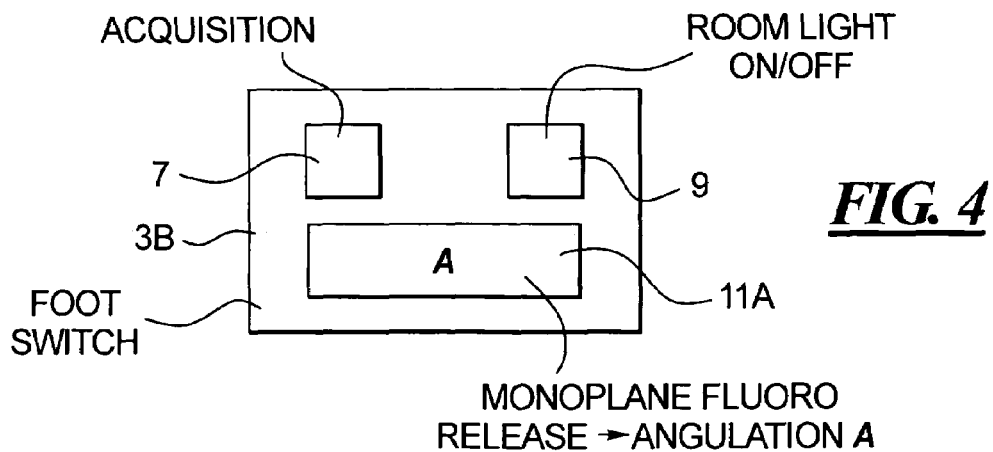
FIG. 4 schematically illustrates another embodiment of a foot switch for use in accordance with the present invention.

As shown in FIG. 4, in another embodiment of the foot switch 3B according to the invention, an input is made to the system control 2 via the user interface 4 to place the system control to place the system control 2 in a "fast angulation" mode. This causes the system control 2 to interpret inputs coming from foot pedals 11a and 9, for example, to automatically move the C-arm to angulation A and angulation B, respectively. In the embodiment of FIG. 4, the monoplane fluoro release foot pedal 11a, in the "fast angulation" mode, becomes the foot pedal that automatically moves the C-arm to angulation A, and the room light on/off foot pedal 9 becomes the foot pedal that automatically causes the C-arm to move to angulation B. After the need for such a temporary reconfiguration or re-programming of the system control to ends, another input can be made via the user interface 4 to restore the foot pedals 11a and 9 to their conventional functions.

Operation of the foot switch 3B is explained in FIG. 5. FIG. 5 tracks the operation described in FIG. 3, with the differences noted below, so that the complete operation need not be repeated.

In an initial step 22 in the embodiment of FIG. 5, the system is set to the "fast angulation" mode by the aforementioned input via the user interface 4, which temporarily reconfigures the room light on/off switch 9 to perform the previously described angulation B function. Preceding the next step 12, the operation is the same as described in connection with FIG. 3, except in steps 17 and 23 the angulation B function is performed by the room light on/off foot pedal 9.

Another example of the manner of using the embodiment 3B is illustrated in the flowchart of FIG. 6. In this embodiment, in step 24 the user presses the fluoro release foot pedal 11a, causing x-rays to be emitted, and in step 25 the user then releases the foot pedal 11a and the angulation B functionality is selected via the user interface 4. In step 26, the user presses the fluoro release foot pedal 11*a* and the system automatically drives to the new position. If the foot pedal 11*a* is released, movement automatically stops.

In step 27, the system 1 has reached the new position, and in step 28 the user again presses the fluoro release foot pedal 11*a*. As indicated in step 29, x-rays are emitted as long the foot pedal 11*a* is pressed. In step 30, the above procedure is repeated, but with a different target angulation, that has been entered via the user interface 4.

In the embodiment of FIG. 6, therefore, instead of another foot pedal, such as the room light on/off switch 9, being temporarily reprogrammed for a different function, the foot pedal 11*a* is successively used first to automatically set angulation A, and then to automatically set angulation B.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system comprising:
    a C-arm having an x-ray source and a radiation receiver mounted thereon, and a drive unit operable to move said C-arm through a plurality of angulation positions;
    a computerized control unit connected to said drive unit; and
    a foot switch connected to said computerized control unit having a plurality of manually operable pedals that provide input commands to said computerized control unit, said pedals including an angulation pedal movable between a first pedal position and a second pedal position, and said computerized control unit being programmed to operate said drive unit to automatically move said C-arm to a programmed, predetermined first angulation position when said angulation pedal is in said first pedal position and to operate said drive unit to automatically move said C-arm to a programmed, predetermined second angulation position when said angulation pedal is in said second pedal position.

2. A medical system as claimed in claim 1 wherein said computerized control unit is programmed, during movement of said C-arm caused by said angulation pedal, to temporarily give said angulation pedal a security function requiring continuous actuation of said angulation pedal in order for said movement of C-arm to continue.

3. A medical system as claimed in claim 2 wherein said computerized control unit, after C-arm has reached either of said first angulation position or said second angulation position, temporarily gives said angulation pedal a radiation trigger function in order to trigger emission of radiation from said x-ray source upon actuation of said angulation pedal.

4. A medical system as claimed in claim 3 wherein said computerized control unit, after said C-arm has reached either of said first angulation position or said second angulation position, automatically temporarily gives said angulation pedal said radiation trigger function.

5. A medical system as claimed in claim 3 wherein said computerized control unit, after said C-arm has reached either said first angulation position or said second angulation position, requires a release and re-actuation of said angulation pedal before temporarily giving said angulation pedal said radiation trigger function.

6. A medical system comprising:
    a C-arm having an x-ray source and a radiation receiver mounted thereon, and a drive unit operable to move said C-arm through a plurality of angulation positions;
    a computerized control unit connected to said drive unit;
    a foot switch connected to said computerized control unit to supply input commands to said computerized control unit, said foot switch including a first pedal and a second pedal;
    a manually operable input unit connected to said computerized control unit to supply further input commands to said computerized control unit, said input unit allowing a user to selectively enter a first input command that places said computerized control unit in a first operating mode, or a second input command that places said computerized control unit in a second operating mode; and
    said computerized control unit being programmed, in each of said first and second operating modes, to operate said drive unit to move said C-arm to a predetermined angulation position upon actuation of said first pedal and, in said first operating mode, to give said second pedal a function unrelated to angulation of said C-arm, and in said second operating mode, to temporarily give said second pedal an angulation function that causes said computerized control unit to operate said drive unit to move said C-arm to a further predetermined angulation position upon actuation of said second pedal.

7. A method for operating a medical system comprising a C-arm having an x-ray source and a radiation receiver mounted thereon, and a drive unit operable to move said C-arm through a plurality of angulation positions, a computerized control unit connected to said drive unit, and a foot switch connected to said computerized control unit having a plurality of manually operable pedals that provide input commands to said computerized control unit, said pedals including an angulation pedal movable between a first pedal position and a second pedal position, said method comprising the steps of:
    programming said computerized control unit by predetermining a first angulation position and a second angulation position;
    with said computerized control unit, operating said drive unit to automatically move said C-arm to said predetermined first angulation position when said angulation pedal is in said first pedal position and operating said drive unit to automatically move said C-arm to said predetermined second angulation position when said angulation pedal is in said second pedal position.

8. A method for operating a medical system as claimed in claim 7 comprising, during movement of said C-arm caused by said angulation pedal, temporarily giving said angulation pedal a security function requiring continuous actuation of said angulation pedal in order for said movement of C-arm to continue.

9. A method for operating a medical system as claimed in claim 8 comprising, through said computerized control unit, after C-arm has reached either of said first angulation position or said second angulation position, temporarily giving said angulation pedal a radiation trigger function in order to trigger emission of radiation from said x-ray source upon actuation of said angulation pedal.

10. A method for operating a medical system as claimed in claim 9 wherein comprising through said computerized control system, after said C-arm has reached either of said first angulation position or said second angulation position, automatically temporarily giving said angulation pedal said radiation trigger function.

11. A method for operating a medical system as claimed in claim 10 comprising through said computerized control system, after said C-arm has reached either said first angulation position or said second angulation position, requiring a release and re-actuation of said angulation pedal before temporarily giving said angulation pedal said radiation trigger function.

12. A method for operating a medical system comprising a C-arm having an x-ray source and a radiation receiver mounted thereon, and a drive unit operable to move said C-arm through a plurality of angulation positions, a computerized control unit connected to said drive unit and, a foot switch connected to said computerized control unit to supply input commands to said computerized control unit, said foot switch including a first pedal and a second pedal, and a manually operable input unit connected to said computerized control unit to supply further input commands to said computerized control unit, said method comprising the steps of:

through said input unit, allowing a user to selectively enter a first input command that places said computerized control unit in a first operating mode, or a second input command that places said computerized control unit in a second operating mode; and with said computerized control unit, in each of said first and second operating modes, operating said drive unit to move said C-arm to a predetermined angulation position upon actuation of said first pedal and, in said first operating mode, giving said second pedal a function unrelated to angulation of said C-arm, and in said second operating mode, temporarily giving said second pedal an angulation function that causes said computerized control unit to operate said drive unit to move said C-arm to a further predetermined angulation position upon actuation of said second pedal.

* * * * *